United States Patent [19]
Kilbourn et al.

[11] 3,994,905
[45] Nov. 30, 1976

[54] 3-PYRIDYLMETHYL ARYL UREA RODENTICIDES

[75] Inventors: Edward E. Kilbourn; David L. Peardon, both of Chalfont; J. Edgar Ware, Quakertown, all of Pa.

[73] Assignee: Rohm and Haas Company, Philadelphia, Pa.

[22] Filed: Oct. 16, 1975

[21] Appl. No.: 622,914

Related U.S. Application Data

[60] Division of Ser. No. 460,264, April 11, 1974, Pat. No. 3,931,203, which is a continuation-in-part of Ser. No. 342,334, March 19, 1973, abandoned.

[52] U.S. Cl................... 260/294.8 F; 260/294.8 C; 260/294.8 G; 260/294.9; 260/295.5 D; 424/84
[51] Int. Cl.².................................. C07D 213/75
[58] Field of Search ............ 260/294.8 G, 294.8 F, 260/294.8 C, 295.5 E

[56] References Cited
UNITED STATES PATENTS

| | | | |
|---|---|---|---|
| 3,284,461 | 11/1966 | Wilbert et al. | 260/295 CA |
| 3,428,642 | 2/1969 | Debay et al. | 260/295 CA |
| 3,584,000 | 6/1971 | Hobart et al. | 260/295.5 C |

FOREIGN PATENTS OR APPLICATIONS 1,071,035   6/1967   United Kingdom.......... 260/295.5 C

*Primary Examiner*—Alan L. Rotman
*Attorney, Agent, or Firm*—William E. Lambert, III

[57] ABSTRACT

Novel 1-(3-pyridylmethyl)-3-(4'-substituted-phenyl or -naphthyl)-ureas and their acid addition salts. The 4'-substituent may be -$NO_2$, -CN, -$CF_3$, -C(O)$R_1$, -SCN, $SR_2$, -$SO_2C_6H_5$ or -$SO_2NR_3R_4$. These compounds are biologically active, and many are active rodenticides.

4 Claims, No Drawings

3-PYRIDYLMETHYL ARYL UREA RODENTICIDES

This is a division of application Ser. No. 460,264 filed Apr. 11, 1974, now U.S. Pat. No. 3,931,203, granted Jan. 6, 1976 which is a continuation-in-part of U.S. Ser. No. 342,334, filed Mar. 19, 1973, now abandoned.

The present invention relates to novel 1-(3-pyridylmethyl)-3-(4'-substituted-phenyl or -naphthyl)ureas and their acid addition salts. These compounds possess desirable biologically active properties, such as bactericidal, fungicidal, herbicidal, insecticidal and rodenticidal properties, but are of particular value as rodenticides.

The common rat, Rattus norvegicus, is vicious and constantly poses a serious threat to the health and well-being of man. Rats and mice are destructive animals and a serious nuisance, causing millions of dollars damage annually to homes, farms, agronomic crops, food processing plants and many other businesses. Rats bite at least 14,000 (possibly up to 60,000) people in the United States every year, according to the U.S. Public Health Service, and are known carriers of over 35 contagious diseases including bubonic plague, trichinosis, typhus, rat bite fever, amoebic dysentery, tuberculosis, infectious jaundice and rabies. During the years from 1898 to 1923, almost 11 million deaths were caused by rat-borne plagues.

Use of rodenticides, fumigants, sprays and traps are the primary methods employed for the control of pest rodents. By "pest rodents" we refer not only to members of the order Rodentia but also to those of Lagomorpha, which cause health hazards or economic loss unless kept in check. Rodenticides may be used in the form of a tracking powder or a bait or may be applied as a spray on the rodent's natural foodstuffs. The rodenticides used as a bait are of two classes: single-dose and multi-dose. Multi-dose rodenticides have usually been preferred to single-dose rodenticides, as they have generally been safer than the single-dose rodenticides heretofore available. The multi-dose rodenticides, such as 4-hydroxy-coumarin and 1,3-indandione compounds, are anti-coagulants generally. These multi-dose rodenticides when consumed in small daily amount have a lethal effect (generally caused by internal bleeding) on rats and mice after depletion of vitamin K stores in the liver. Anti-coagulant types of rodenticides are less effective on mice than rats, as mice are considered to be nibblers and do not usually consume an adequate amount of treated bait to have a lethal effect. A single-dose rodenticide which would be relatively safe to the person handling the material and to non-target species of animals and yet effective on a variety of pest rodents is highly desirable.

Many compounds are toxic to rodents. However, very few of these compounds are anywhere near suitable for use as a rodenticide because it is necessary for the pest rodent to consume voluntarily a sufficient amount of the poison even though sufficient untreated food may also be available. In rodenticides used as bait or as a spray, feed acceptance is the key to excellence, and in all rodenticides safety and efficacy are highly important.

The 1-(3-pyridylmethyl)-3-(4'-substituted-phenyl or -naphthyl)ureas of the present invention are so highly toxic to a wide variety of pest rodents that a single dose is sufficient; yet many of them are relatively safe for use in the presence of other species which may inadvertently ingest limited quantities of the rodenticide. Furthermore, rats and other pest rodents willingly consume the compounds of the present invention in sufficiently lethal amounts when present in baits. Alternatively, the compounds may be employed in compositions to be sprayed on natural foodstuffs. They may also be employed in tracking powder, especially for use against mice, which habitually clean their paws by licking.

The compounds of the present invention have the formula:

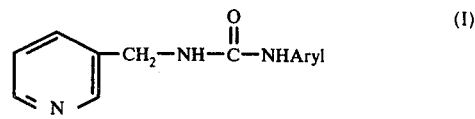

wherein Aryl is

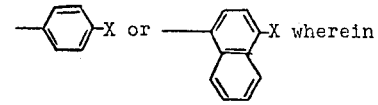

X is selected from the group consisting of $-NO_2$, $-CN$, $-CF_3$, $-C(O)R_1$ wherein $R_1$ is methyl, ethyl or propyl, $-SR_2$ wherein $R_2$ is hydrogen, cyano or alkyl of 1 to 6 carbon atoms or $-SO_2Y$ wherein Y is $-C_6H_5$ or $-NR_3R_4$ wherein $R_3$ and $R_4$ are hydrogen, methyl or ethyl, The acid addition salts of these novel 3-pyridylmethyl aryl ureas are also included.

Of these compounds, the preferred ones are those in which Aryl is

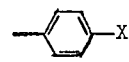

and especially those in which X is $-C(O)CH_2CH_2CH_3$, $-CN$, $-NO_2$ or $-SCH_3$. The most preferred compound is 1-(3-pyridylmethyl)-3-(4-nitrophenyl)urea.

It is to be noted that the X-substituents on the phenyl or naphthyl ring are highly electron-withdrawing except for the $-SR_2$ groups.

The literature is rather sparse with respect to 1-(3-pyridylmethyl)-3-(aryl)ureas which are frequently named 1-(3-picolyl)-3-(aryl)ureas. Hamilton and Sculley in J. American Chemical Soc. 75, 3400(1953) reported on the chemistry of a 1-(3-picolyl)-3-phenylurea having various substituents on the picolyl nucleus. U.S. Pat. No. 3,700,678 is concerned with 1-methyl-1-picolyl-3-aryl ureas useful for controlling undesirable vegetation.

The ureas of the present invention may be prepared by permitting approximately equimolar amounts of substituted-phenyl isocyanate and 3-aminomethylpyridine to react in the presence of an inert solvent, e.g., acetonitrile, benzene, toluene or 1,2-dimethyoxyethane (glyme). Examples 1, 4 and 11 describe the preparation of compounds of the present invention in this manner. Table I below gives the physical constants for the aryl isocyanate intermediates (which are made from the corresponding X-substituted anilines) used in their preparation.

Table I

| Aryl-NCO Intermediates | | |
|---|---|---|
| Used in Example | Aryl= | Melting point (° C) or Boiling point (° C/pressure mm.) |
| 1 | —$C_6H_4NO_2$-4 | a commercial product |
| 3 | —$C_6H_4CF_3$-4 | 78–79/20 |
| 4 | —$C_6H_4SH$-4 | 56–61/0.85 |
| 5 | —$C_6H_4SCN$-4 | oil[a] |
| 6 | —$C_6H_4SCH_3$-4 | 68/0.15 |
| 7 | —$C_6H_4SC_2H_5$-4 | 52–60/0.3 |
| 8 | —$C_6H_4(SC_3H_7$-n$)$-4 | 53–54/0.25 |
| 9 | —$C_6H_4(SC_4H_9$-n$)$-4 | 105–109/0.35 |
| 10 | —$C_6H_4(SC_4H_9$-sec$)$-4 | 110/0.25 |
| 11 | —$C_6H_4(SC_4H_9$-t$)$-4 | 86/0.45 |
| 12 | —$C_6H_4(SC_6H_{13}$-n$)$-4 | 112–117/0.25 |
| 13 | —$C_6H_4C(O)CH_3$-4 | oil[a] |
| 14 | —$C_6H_4C(O)CH_2CH_3$-4 | oil[a] |
| 15 | —$C_6H_4C(O)CH_2CH_2$—$CH_3$-4 | oil[a] |
| 16 | —$C_6H_4SO_2C_6H_5$-4 | 123–126 |
| 17 | —$C_6H_4SO_2N(C_2H_5)_2$-4 | 150–153/0.3 |
| 18 | 4-nitronaphthyl | oil[a] |

[a]identified by infrared spectra - all giving a strong —N=C=O band at 4.3 to 4.6$\mu$.

Alternatively the ureas may be prepared by permitting approximately equimolar amounts of the X-substituted aniline and a carbamate, such as phenyl N-(3-pyridylmethyl)-carbamate, to react in a polar solvent such as ethanol. Example 2 describes the preparation of one of the compounds of the present invention in this manner.

The novel 3-pyridylmethyl aryl ureas of this invention are basic and can form acid addition salts with a strong inorganic or organic acid. Typical acids which form such salts include hydrobromic, hydrochloric, hydrofluoric, nitric, phosphoric, sulfuric, chloroacetic, oxalic, maleic, succinic, tartaric and p-toluenesulfonic. Of these salts the hydrochloride is preferred. A typical preparation of such a salt is described below for Example 19.

EXAMPLE 1

Preparation of
1-(3-pyridylmethyl)-3-(4-nitrophenyl)urea

A solution of 415 g. of crude p-nitrophenyl isocyanate in 4.5 l. of toluene was stirred at room temperature. The mixture was filtered and 35 g. of insoluble impurity removed. The material in solution was 380 g. (2.32 mol) of purified p-nitrophenyl isocyanate. The solution was stirred under dry nitrogen, and 3-(aminomethyl)pyridine (250 g., 2.32 mol) was added dropwise. An exotherm to 40° C. was noted. The resulting thick suspension was stirred overnight and then vacuum filtered. The product was washed with hexane and dried in a vacuum oven at 60° C. overnight to give 610.7 g. melting at 220°–221.5° C. The product was a 98% yield of 1-(3-pyridylmethyl)-3-(4-nitrophenyl)urea. This product after recrystallization from 2-methoxyethanol melted with decomposition at 223°–225° C.

EXAMPLE 2

Preparation of
1-(3-pyridylmethyl)-3-(4-cyanophenyl)urea

The intermediate phenyl N-(3-pyridylmethyl)-carbamate was prepared as follows:

A solution was prepared of 3-aminomethylpyridine (21.6 g., 0.2 mol) and triethylamine (22.2 g., 0.2 mol) in 150 ml. of anhydrous ether. A solution of phenyl chloroformate (31.4 g., 0.2 mol) in 100 ml. of dry ether was added dropwise in 20 minutes. The resultant suspension was stirred for 30 more minutes, then was vacuum-filtered to remove triethylamine hydrochloride. The filtrate, when cooled, gave 4.1 g. of the desired carbamate melting at 88°–90° C. The second filtrate, when evaporated, afforded 25 g. of the product in a slightly impure condition melting at 75°–85° C. The triethylamine hydrochloride was dissolved in water, and the aqueous solution was then extracted with methylene dichloride. The dried methylene dichloride extract was evaporated to give 11 g. of product melting at 82°–85° C. Total crude yield of phenyl N-(3-pyridylmethyl)carbamate was 40.1 g. or 89%.

The urea was then prepared from the carbamate as follows:

To a solution of phenyl N-(3-pyridylmethyl)-carbamate (10.9 g., 0.05 mol) in 150 ml. of anhydrous ethanol there was added p-aminobenzonitrile (5.7 g., 0.05 mol). The mixture was refluxed for 5 hours, cooled, and evaporated under reduced pressure to yield a dark oil. This oil was dissolved in ether, and this solution was washed three times with 50 ml. portions of 5% NaOH. After drying of the ether solution and evaporation of the solvent, a yellow oil was obtained which was placed under high vacuum. A small quantity of material sublimed while the residue in the flask crystallized. Recrystallization from ethyl acetate gave 5.2 g. of white crystals melting at 184°–187° C. This was a 43% yield of 1-(3-pyridylmethyl)-3-(4-cyanophenyl)urea.

EXAMPLE 4

Preparation of
1-(3-pyridylmethyl)-3-(4-mercaptophenyl)urea a. Preparation of 4-mercaptophenyl isocyanate A reaction mixture consisting of molar quantities of t-butylmercaptan, potassium hydroxide and p-chloronitrobenzene in 1.2 l. of ethanol was stirred for 4 days at room temperature to 45° C and then filtered. The filtrate was poured into water and extracted with methylene dichloride to give 161 g. of a brown oil which is a 76% weight yield of crude 4-(t-butylmercapto)nitrobenzene.

To a suspension of 4-(t-butylmercapto)nitrobenzene (52.8 g., 0.25 mol) and iron powder (150 g.) in 1 l. of water there was added 1 ml. of acetic acid. The reaction mixture was stirred 18 hours at 90° C. and filtered. Both the residue and filtrate were extracted several times with methylene dichloride, and the combined dried methylene dichloride extracts were concentrated at reduced pressure to give 18.2 g. of a brown oil. This is a 40% weight yield of 4-(t-butylmercapto)aniline. To this oil in 100 ml. of benzene there was then added dropwise 158 g. of a 12.5% benzene solution of phosgene (0.2 mol) with cooling. The reaction mixture was stirred for 1 hour at 10° C., overnight at room temperature and then at reflux temperature for 7 hours. After standing overnight the reaction mixture was filtered, the filtrate concentrated at reduced pressure, then vacuum-distilled. Two product fractions were collected as 1. 2 g. distilling at 56°–61° C./0.85 mm. and
2. 2 g. distilling at 86° C./0.45 mm.

Fraction 1 is 4-mercaptophenyl isocyanate and Fraction 2 is 4-(t-butylmercapto)phenyl isocyanate.

b. Preparation of 1-(3-pyridylmethyl)-3-(4-mercaptophenyl)urea

To 4-mercaptophenyl isocyanate (0.9 g., 0.006 mol) in 50 ml. of anhydrous benzene was added 3-pyridylmethylamine (0.65 g., 0.006 mol). An exothermic reaction caused the temperature to rise to 40° C. and a white precipitate formed. The reaction mixture was momentarily heated to reflux, then cooled to room temperature and filtered to give 1.2 g. melting at 155°–159° C. The product was a 77.5% yield of 1-(3-pyridylmethyl)-3-(4-mercaptophenyl)urea.

EXAMPLE 11

Preparation of 1-(3-pyridylmethyl)-3-(4-t-butylmercaptophenyl)urea

To 4-(t-butylmercapto)phenyl isocyanate (1 g., 0.005 mol; see Example 4 above) in 50 ml. of anhydrous benzene there was added 3-pyridylmethylamine (0.52 g.. 0.005 mol). The temperature rose to 40° C. and a precipitate formed. The reaction mixture was heated to reflux for a very short time then cooled and filtered to give 1.5 g. of solid melting at 154°–157.5° C. The product was a 98% yield 1-(3-pyridylmethyl)-3-(4-t-butylmercapto)phenylurea.

EXAMPLE 19

Preparation of 1-(3-pyridylmethyl)-3-(4-nitrophenyl)urea hydrobromide.

Gaseous HBr was passed into a solution of 3 g. of 3-pyridylmethyl-3-(4-nitrophenyl)urea in the monomethyl ether of ethyleneglycol. Ether was added to give a precipitate and after isolation, washing with ether and drying, 2.95 g. of white solid was obtained. This was a 76% yield of 1-(3-pyridylmethyl)-3-(4-nitrophenyl)urea hydrobromide.

Table II, concerning "3-PyridylCH$_2$NHC(O)NHAryl-X Compounds," gives the physical constants and analytical data for typical examples of this invention. In this table the column headings have the following meanings: Ex. is Example No., X is the 4-substituent in the phenyl nucleus (or naphthyl for Example 18), M.P. is Melting Point ("dec." with decomposition), Emp. Form. is Empirical Formula and "%C," "%H" and "%N" are analytical data (the number in parentheses represents the theoretical value as calculated from the empirical formula).

Table II

3-Pyridyl-CH$_2$NHC(O)NH-Aryl-X Compounds

| Ex. | X= | M.P. (° C) | Emp. Form. | % C | % H | % N |
|---|---|---|---|---|---|---|
| 1 | NO$_2$-4 | 223–225 (dec.) | C$_{13}$H$_{12}$N$_4$O$_3$ | 57.1 (57.3) | 4.2 (4.4) | 20.8 (20.6) |
| 2 | CN-4 | 184–187 | C$_{14}$H$_{12}$N$_4$O | 66.4 (66.7) | 4.9 (4.8) | 21.9 (22.2) |
| 3 | CF$_3$-4 | 176–178.5 | C$_{14}$H$_{12}$F$_3$N$_3$O | 57.0 (57.0) | 4.0 (4.1) | 14.1 (14.2) |
| 4 | SH-4 | 155–159 | C$_{13}$H$_{13}$N$_3$OS | 59.9 (60.2) | 4.8 (5.0) | 16.0 (16.2) |
| 5 | SCN-4 | 153.5–155.5 | C$_{14}$H$_{12}$N$_4$OS | 59.6 (59.1) | 4.3 (4.3) | 19.6 (19.7) |
| 6 | SCH$_3$-4 | 148–150 | C$_{14}$H$_{15}$N$_3$OS | 61.4 (61.5) | 5.6 (5.5) | 15.5 (15.4) |
| 7 | SC$_2$H$_5$-4 | 140–143 | C$_{15}$H$_{17}$N$_3$OS | 62.5 (62.7) | 5.8 (6.0) | 14.6 (14.6) |
| 8 | (SC$_3$H$_7$-n)-4 | 130–133 | C$_{16}$H$_{19}$N$_3$OS | 64.0 (63.8) | 6.4 (6.4) | 13.9 (13.9) |
| 9 | (SC$_4$H$_9$-n)-4 | 36–137 | C$_{17}$H$_{21}$N$_3$OS | 64.8 (64.7) | 6.6 (6.7) | 13.5 (13.3) |
| 10 | (SC$_4$H$_9$-sec.)-4 | 141–144.5 | C$_{17}$H$_{21}$N$_3$OS | 64.7 (64.7) | 6.5 (6.7) | 13.6 (13.3) |
| 11 | (SC$_4$H$_9$-t)-4 | 154–157.5 | C$_{17}$H$_{21}$N$_3$OS | 64.5 (64.7) | 6.8 (6.7) | 13.5 (13.3) |
| 12 | (SC$_6$H$_{13}$-n)-4 | 117–119 | C$_{19}$H$_{25}$N$_3$OS | 66.3 (66.5) | 7.2 (7.3) | 12.6 (12.2) |
| 13 | C(O)CH$_3$-4 | 142–143 | C$_{15}$H$_{15}$N$_3$O$_2$ | 66.7 (66.9) | 5.4 (5.6) | 15.8 (15.6) |
| 14 | C(O)CH$_2$CH$_3$-4 | 157–159 | C$_{16}$H$_{17}$N$_3$O$_2$ | 67.2 (67.8) | 6.0 (6.1) | 14.7 (14.8) |
| 15 | C(O)CH$_2$CH$_2$CH$_3$-4 | 168–170.5 | C$_{17}$H$_{19}$N$_3$O$_2$ | 68.3 (68.7) | 6.4 (6.4) | 13.9 (14.1) |
| 16 | SO$_2$C$_6$H$_5$-4 | 198–201 | C$_{19}$H$_{17}$N$_3$O$_3$S | 62.2 (62.1) | 4.7 (4.7) | 11.3 (11.4) |
| 17 | SO$_2$N(C$_2$H$_5$)$_2$-4 | 122–124.5 | C$_{17}$H$_{22}$N$_4$O$_3$S | 56.1 (56.3) | 6.0 (6.1) | 15.3 (15.5) |
| 18 | (4-NO$_2$naphthyl) | 221–223 (dec.) | C$_{17}$H$_{14}$N$_4$O$_3$ | 63.4 (63.4) | 4.4 (4.4) | 17.1 (17.4) |
| 19 | HBr salt of Example 1 | 235–240 | C$_{13}$H$_{12}$N$_4$O$_3$ . HBr | 43.8 (44.0) | 3.5 (3.7) | 15.8 (15.8) |
| 20 | HCl salt of Example 1 | 255–260 | C$_{13}$H$_{12}$N$_4$O$_3$ . HCl | 50.7 (50.6) | 4.0 (4.2) | 20.1 (18.1) |
| 21 | p-Toluenesulfonic acid salt of Example 1 | 201–204.5 | C$_{13}$H$_{12}$N$_4$O$_3$ . 4-CH$_3$C$_6$H$_4$SO$_3$H | 54.0 (54.0) | 5.0 (4.5) | 13.1 (12.6) |
| 22 | Oxalic acid salt of Example 1 | 210–211 (dec.) | C$_{13}$H$_{12}$N$_4$O$_3$ . (—COOH)$_2$ | 49.9 (49.7) | 5.0 (3.9) | 16.3 (15.5) |
| 23 | Malonic acid salt of Example 1 | 130–134 (dec.) | C$_{13}$H$_{12}$N$_4$O$_3$ . CH$_2$(COOH)$_2$ | 51.0 (51.1) | 4.7 (4.3) | 13.9 (14.9) |
| 24 | Tartaric acid salt of Example 1 | 166–170 (dec.) | C$_{13}$H$_{12}$N$_4$O$_3$ . (—CHOH—COOH)$_2$ | 48.2 (48.3) | 4.3 (4.3) | 13.0 (13.3) |
| 25 | HCl salt of Example 2 | 208–210 (dec.) | C$_{14}$H$_{12}$N$_4$O . HCl monohydrate | 54.6 (54.8) | 4.4 (4.9) | 18.5 (18.3) |
| 26 | Oxalic acid salt of Example 2 | 227–229 (dec.) | C$_{28}$H$_{24}$N$_8$O$_2$ . (—COOH)$_2$ | 60.0 (60.6) | 4.8 (4.4) | 18.8 (18.9) |
| 27 | HCl salt of Example 3 | 186–188 (dec.) | C$_{14}$H$_{12}$F$_3$N$_3$O . HCl | 50.7 (50.7) | 3.9 (4.0) | 12.8 (12.7) |

Table II-continued

| | | 3-Pyridyl-CH₂NHC(O)NH-Aryl-X Compounds | | | | |
|---|---|---|---|---|---|---|
| Ex. | X= | M.P. (° C) | Emp. Form. | % C | % H | % N |
| 28 | HCl salt of Example 15 | 179–181 (dec.) | C₁₇H₁₉N₃O₂ . HCl hemihydrate | 59.5 (59.6) | 6.1 (6.2) | 12.3 (12.3) |
| 29 | Oxalic acid salt of Example 15 | 75–80 (dec.) | C₁₇H₁₉N₃O₂ . (—COOH)₂ monohydrate | 56.7 (56.3) | 5.6 (5.7) | 10.2 (10.4) |

The novel 1-(3-pyridylmethyl)-3-aryl ureas of the invention are biologically active and may be useful as bactericides, fungicides especially for phytopathogenic fungi, insecticide, rodenticides and herbicides.

The following description describes the use of the compounds of the invention as a rodenticide.

Formulation for use as a rodenticide

The compounds of the present invention may be formulated into rodenticidal compositions such as baits, tracking powders, and sprays. A bait may, besides the toxicant, comprise a basal ration, such as a carrier usually edible optionally with a preservative to prevent insect infestation, mold growth or rancidity. A rodent's taste for food varies according to the locality where he lives. The compounds of the present invention may be formulated with any edible carrier which is preferred by the rodents in the specific area where the rodenticide is to be applied. The carrier may be a semi-moist material, such as canned cat or dog food or garbage including apples, eggs, bacon, etc., but it is generally preferred to use a dry carrier as this remains acceptable for longer periods. The dry carrier may be a combination of natural food products such as whole ground corn, steel cut oats, sugar, molasses, rice, vegetable oil, salt, dehydrated fruit, fish meal, tankage or wheat. When necessary to use damp locations, the basal ration may include a binder to form the composition into a matrix. The binder may be a water repellent material, such as a paraffin wax or an acrylic polymer.

The compounds of the present invention may be incorporated as a toxicant in bait formulations, either alone or in combination with other toxicants. When used as the sole toxicant in baits, the compounds of the present invention may be used in any rodenticidally effective concentration.

Depending on the susceptibility of the rodents to the toxicant and the amount of formulated bait generally consumed, concentrations as low as 0.01% may be employed. A typical bait may contain between about 0.5% and 2.5% of the toxicant by weight. It has been found that there is no upper limit to the amount of compound which may be present in a bait and that a bait consisting almost entirely of one of the present compounds can be ingested in a rodenticidally sufficient quantity. The formulated bait will generally contain the active ingredient in the range of 0.5 to 99.5% by weight. Example 30 describes the formulation of a suitable bait, although wide variations in formulation may be made for different conditions of use.

Tracking powders, which are particularly effective against mice, may be either a compound of the present invention in finely powdered form or a mixture of the compound with a powdered carrier, e.g., talc, milk mild powder, Indian corn meal, fish meal, cornstarch, flour, and bentonite, or the like, or any combination thereof which tends to induce the animals contaminated with the preparation to lick themselves more thoroughly. In tracking powders, the compounds of the present invention may be incorporated in amounts from 99.5% down to 0.5% by weight, or somewhat less with proper formulation. Example 31 describes the preparation of a suitable tracking powder.

Spray concentrations may be made by dissolving the compounds of this invention in a solvent. In general, the 1-(3-pyridylmethyl)-3-aryl ureas have a limited solubility, i.e. between 1 and 15%. Solvents which are useful for making a spray strength solution include alcohols such as ethanol and 2-methoxyethanol, ketones such as acetone, dimethylformamide, dimethyl sulfoxide and pyridine. The acid addition salts have increased solubility in protonated solvents. In certain instances, notably the hydrochloride salts, at least a 25% solution in water and a 40% solution in 2-methoxyethanol can be made. In general a rather volatile solvent is preferred when a solution is to be sprayed onto a natural food source of the rodents, so that the solvent will be rather rapidly removed and the toxicant is deposited in an essentially unadulterated form onto the food.

These rodenticidal compounds in the proper form would be placed in the pathway or vicinity where the rodents are expected to travel, in most instances near a source of food and water, and would after be caged to prevent interference by larger animals.

EXAMPLE 30

Bait Formulation

Each of the compounds of Examples 1 to 29 was blended with the basal ration in a Waring laboratory blender to form 50 grams of a homogeneous premix. The amount of compound utilized is determined by the percentage of active material desired in the feed. The formula for the basal ration is shown below, all percentages being by weight:

| | |
|---|---|
| Crude ground corn | 65% |
| Steel cut oats | 25% |
| Powdered sugar | 5% |
| Corn oil | 5% |

The 50 grams of premix containing the toxicant were then mixed with an additional 450 grams of basal ration. These components are mixed in a Little Ford Lodge mixer for 3 minutes.

EXAMPLE 31

Tracking Powder

The active compound is finely pulverized by mortar and pestle to form a 100%-active tracking powder. To form a 5% active material, it may be mixed with 10X confectioner's sugar in a 1 to 19 ratio and at other ratios for other levels of active compound.

Rodenticidal evaluations a. Preliminary evaluations

One preliminary evaluation is on the albino mouse, (*Mus musculus*). In such a test, four caged laboratory albino mice are fed a diet containing the test compound at 1000 parts per million (ppm) for 14 days. On each of the 11th, 12th and 13th days there is also orally administered to the surviving mice, the toxicant in a 0.5% aqueous methyl cellulose solution at a dosage of 200 mg./kg. The number of mice that died up through the 10th day of feeding and the total that died during the 14-day test period were recorded.

The compounds were preliminarily evaluated for their ability to kill albino rats (*Rattus norvegicus*) by oral administration to two rats at a dosage of 50 mg./kg. and sometimes at 200 mg./kg. The effect on the rats was observed 14 days later. If at least one of the rats had died, the compound was then subjected to secondary tests. Table III gives the results.

Table III

| | Preliminary Rodenticidal Activity Acute Oral Toxicity | | | |
|---|---|---|---|---|
| | Albino mice | | Albino rats | |
| Example | fed 10 days on 1000 ppm | + oral dosage for 3 days at 200 mg./kg. | 50 mg/kg | 200 mg/kg |
| 1 | 1/4 | 4/4 | 2/2 | |
| 2 | 2/4 | 4/4 | 2/2 | |
| 3 | 0/4 | 2/4 | 1/2 | |
| 4 | 0/4 | 0/4 | 0/2 | |
| 5 | | | 1/2 | 0/2 |
| 6 | 0/4 | 1/4 | 1/2 | |
| 7 | 0/4 | 0/4 | 0/2 | 1/2 |
| 8 | 0/4 | 0/4 | 0/2 | 0/2 |
| 9 | 1/4 | 3/4 | 0/2 | 0/2 |
| 10 | 3/4 | 3/4 | 0/2 | 0/2 |
| 11 | 0/4 | 0/4 | 0/2 | 0/2 |
| 12 | 4/0 | — | 1/2 | |
| 13 | — | — | 0/2 | — |
| 14 | 0/4 | 0/4 | 0/2 | |
| 15 | 4/0 | — | 2/2 | |
| 16 | 0/4 | 0/4 | 1/2 | |
| 17 | 0/4 | 2/4 | 1/2 | |
| 18 | — | — | 1/2 | |
| 19 | | | 2/2 | |
| 20 | | | 2/2 | |
| 21 | | | 2/2 | 2/2 |
| 22 | | | 1/2 | |
| 23 | | | 2/2 | |
| 24 | | | 2/2 | |
| 25 | | | | |
| 26 | | | 2/2 | |
| 27 | | | 0/2 | |
| 28 | | | 2/2 | |
| 29 | | | 2/2 | |

*Data given as rodents killed/rodents tested b. Secondary evaluations

One of the most significant secondary tests is a standard one known as the paired-preference test. In this test the rodents are given a free choice between the treated and untreated bait. Such a test most nearly approximates practical use conditions.

The rodents were caged individually, and were provided with dual feed cups and separate water devices. The basal ration was offered in excess of daily feed requirements in each of two feeders: one treated with the test compound and one without. For each test, equal numbers of each sex were used.

The gross weight of each feed container and its feed were determined daily and returned to the starting weight by addition of complete replacement of the given diet. The position of the bait and the laboratory diet cups in the cage were reversed every 24 hours to counter any feeding position habit of the rat. The test rodents had free choice between treated and untreated feed. Mortalities were recorded daily.

To meet the criteria for a single-dose product, a rodenticide in this initial test must kill 75% of the rats within 8 days, where the poison bait is available for the first 72 hours of this period.

The results of representative paired-preference tests with several examples on individually-caged rodents are given in Table IV.

TABLE IV

| | Paired-Preference Tests | | |
|---|---|---|---|
| Example | Rodent | Compound in Basal Ration (ppm) | Rodents killed/ Rodents tested |
| 1 | albino rat (*Rattus norvegicus*) | 100,000 | 1/4 |
| | | 50,000 | 1/2 |
| | | 10,000 | 2/2 and 3/4 |
| | | 3,000 | 2/2 |
| | | 1,000 | 1/2 and 1/4 |
| | | 500 | 0/2 |
| | | 100 | 3/4 |
| 1 | Norway rat (*Rattus norvegicus*) | 10,000[a] | 9/10[a] |
| 1 | roof rat (*Rattus rattus*) | 10,000 | 3/4 |
| 1 | feral mouse (*Mus musculus*) | 10,000[b] | 1/4 |
| | | 10,000[c] | 4/4 |
| 1 | deer mouse (*Peromyscus pennsylvanicus*) | 10,000 | 4/4 |
| 1 | meadow vole (*Microtus leucopus*) | 10,000 | 0/4 |
| 2 | albino rat | 3,000 | 1/2 |
| 3 | albino rat | 3,000 | 0/2 |
| 6 | albino rat | 50,000 | 1/2 |
| | | 10,000 | 2/2 |
| | | 3,000 | 1/2 |
| 17 | albino rat | 3,000 | 0/2 |

[a] This evaluation was run as a one-day, single-bowl test.
[b] This bait used the product of Example 1 melting at 220–221.5° C.
[c] This bait used the product of Example 1 melting at 223–225° C.

When evaluated by the preliminary evaluation technique described above, the following structures very closely related to the highly active Example 1, 1-(3-pyridylmethyl)-3-(4-nitrophenyl)urea, were devoid of activity:

1-(2-pyridylmethyl)-3-(4-nitrophenyl)urea
1-(4-pyridylmethyl)-3-(4-nitrophenyl)urea
1-(3-pyridylmethyl)-3-(4-nitrophenyl)thiourea
1-methyl-1-(3-pyridylmethyl)-3-(4-nitrophenyl)urea
1-(3-pyridylmethyl)-3-methyl-3-(4-nitrophenyl)urea It is concluded that a very exacting structure is required to achieve excellent rodenticidal activity.

It is to be understood that changes and variations may be made without departing from the spirit and scope of the invention as defined herein.

We claim:

1. A compound, or an acid addition salt thereof, having the formula

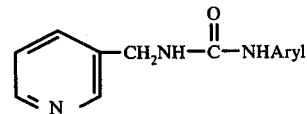

wherein Aryl is

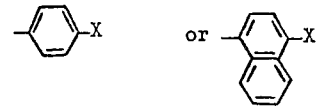

wherein X is selected from the group consisting of -SR$_2$ wherein R$_2$ is hydrogen or cyano or alkyl of 1 to 6 carbon atoms, and -SO$_2$Y wherein Y is -C$_6$H$_5$ or -NR$_3$R$_4$ wherein R$_3$ and R$_4$ are hydrogen, methyl or ethyl.

2. A compound according to claim 1 wherein X is -SCH$_3$.

3. The compound according to claim 2 wherein the acid addition salt is the hydrochloride.

4. A compound according to claim 1 wherein Aryl is

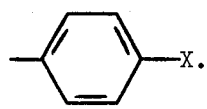

* * * * *